(12) United States Patent
Aravamudan

(10) Patent No.: US 9,282,938 B2
(45) Date of Patent: Mar. 15, 2016

(54) RADIOLUCENT PATIENT TABLE

(71) Applicant: Gosakan Aravamudan, Bangalore (IN)

(72) Inventor: Gosakan Aravamudan, Bangalore (IN)

(*) Notice: Subject to any disclaimer, the term of this patent is extended or adjusted under 35 U.S.C. 154(b) by 0 days.

(21) Appl. No.: 14/709,485

(22) Filed: May 12, 2015

(65) Prior Publication Data

US 2015/0327819 A1    Nov. 19, 2015

(51) Int. Cl.
*A61G 13/00*    (2006.01)
*A61B 6/04*    (2006.01)
*A61G 13/10*    (2006.01)

(52) U.S. Cl.
CPC ............. *A61B 6/0442* (2013.01); *A61G 13/10* (2013.01)

(58) Field of Classification Search
CPC ....................................................... A61G 13/00
USPC ................ 5/600–601; 378/208–209; 600/415
See application file for complete search history.

(56) References Cited

U.S. PATENT DOCUMENTS

| 4,956,885 A * | 9/1990 | Alich et al. ................. 5/601 |
| 7,484,253 B1 * | 2/2009 | Coppens ..................... 5/601 |
| 2006/0185087 A1 * | 8/2006 | Coppens et al. ............. 5/601 |

* cited by examiner

*Primary Examiner* — Fredrick Conley
(74) *Attorney, Agent, or Firm* — Ash Tankha; Lipton, Weinberger & Husick

(57) ABSTRACT

A radiolucent patient table top including a first face sheet, a second face sheet, and a honeycomb core is provided. The first face sheet includes carbon fibers in a first radiolucent plastic matrix. The second face sheet includes carbon fibers in a second radiolucent plastic matrix. The honeycomb core is disposed between the first face sheet and the second face sheet, where the first face sheet and the second face sheet sandwich the honeycomb core. The honeycomb core includes carbon fibers embedded in a third radiolucent plastic matrix.

3 Claims, 3 Drawing Sheets

RADIOLUCENT PATIENT TABLE

CROSS-REFERENCE TO RELATED APPLICATIONS

This application claims priority to and the benefit of provisional patent application number 2424/CHE/2014 titled "Radiolucent Patient Table", filed in the Indian Patent Office on May 15, 2014, and non-provisional patent application number 2424/CHE/2014 titled "Radiolucent Patient Table", filed in the Indian Patent Office on May 11, 2015. The specifications of the above referenced patent applications are incorporated herein by reference in their entirety.

BACKGROUND

The apparatus disclosed herein, in general, relates to a composite structure, and more specifically, relates to a radiolucent patient table top.

Conventional radiolucent patient tables comprise carbon fiber reinforced plastic (CFRP) skins with a foam core made of, for example, polyurethane or polymethacrylimides. CFRP table tops have twice as much X-ray permissibility as wooden table tops and five times that of plastic table tops. Improved radiolucency results in reducing a dosage of X-rays and associated health risks to a patient. The challenges associated with using a foam core in conventional radiolucent patient table tops are described below.

It is well known that the relative strength of composite skins made from foam cores is low when compared to the relative strength of honeycomb sandwich structures. Foam core sandwich structures have less fatigue resistance, and may structurally weaken over repeated loading and unloading of a patient table. Hence, manufacturers typically recommend a permissible working life period for these tables, after which they need to be replaced.

The radiolucent property of a foam core is less than that of carbon, and there is a possibility of contamination in the foam core made of polyurethane that may show up as errors during X-ray examination. The volume and amount of material in the table top must be reduced to a minimum. Non-radiolucent foreign material in the table top can result in a misdiagnosis of the patient.

Some X-ray table tops or their accessory components are made of thick sheets of carbon laminates. There is a need to reduce the quantity of carbon fibers and epoxy binders typically used in X-ray table tops to improve their permissibility to X-rays. Therefore, there is a need for low density carbon fiber table tops that are more radiolucent, that is, more permissible to X-rays.

Moreover, in an X-ray machine, the X-ray table top is required to be steady and therefore stiff in the field of detectors. The cantilever nature of an X-ray table exerts demanding loading on the X-ray table top. Foam core sandwich structures have poorer relative strength and stiffness when compared to honeycomb sandwich structures. In the aerospace industry, for structural applications, honeycomb cores are strongly preferred over foam cores. To improve stiffness, cantilevered foam core table tops have to be made thick. However, such thick table tops interfere with the easy maneuverability of the table tops, and therefore structural and ergonomic design compromises need to be made.

Hence, there is a long felt but unresolved need for a radiolucent patient table top that addresses the above mentioned problems of fatigue, increased thickness, reduced stiffness, and the need to reduce dosage of X-rays by improved radiolucency performance.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The radiolucent patient table top disclosed herein addresses the above mentioned problems of fatigue, increased thickness, and reduced stiffness, and addresses the need to reduce dosage of X-rays by improved radiolucency performance. The radiolucent patient table top disclosed herein comprises a first face sheet, a second face sheet, and a carbon fiber honeycomb core. The first face sheet comprises carbon fibers in a first radiolucent plastic matrix. The second face sheet comprises carbon fibers in a second radiolucent plastic matrix. The honeycomb core is disposed between the first face sheet and the second face sheet. The first face sheet and the second face sheet sandwich the honeycomb core. The honeycomb core comprises carbon fibers embedded in a third radiolucent plastic matrix.

The carbon fiber honeycomb core disclosed herein has improved radiolucency performance over existing foam core solutions. Hence, the X-ray dosage to the patient can be reduced as a lower X-ray intensity is sufficient for the X-ray scan.

The strength to weight ratio of the face sheets and the carbon fiber honeycomb core disclosed herein is high due to the increased stiffness of the carbon fibers in the honeycomb core. The crush strength and fatigue performance of honeycomb sandwich structures are substantially higher than that of comparable foam core structures. Hence, the total weight for a given strength performance, that is, the material present in the radiolucent patient table top is lesser compared to that of conventional foam core solutions. Furthermore, less material consumed minimizes a risk of contamination by radiolucence of foreign materials.

The strength to weight ratio of the sandwich structure disclosed herein, that is, the carbon fiber reinforced first face sheet and second face sheet sandwiching the carbon fiber reinforced honeycomb core, is substantially higher than solid carbon sheet table tops. Hence, the total weight of the material present in the radiolucent patient table top is lesser compared to that of conventional solid carbon sheet table top solutions.

For an equivalent stiffness performance, the radiolucent patient table top disclosed herein is thinner than the known foam core sandwich structures. Thinner radiolucent patient table tops improve maneuverability of the radiolucent patient table tops, resulting in an improved ergonomic design. A stiffer radiolucent patient table top yields a more stable image in a detector field.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF THE INVENTION

Figure 1:
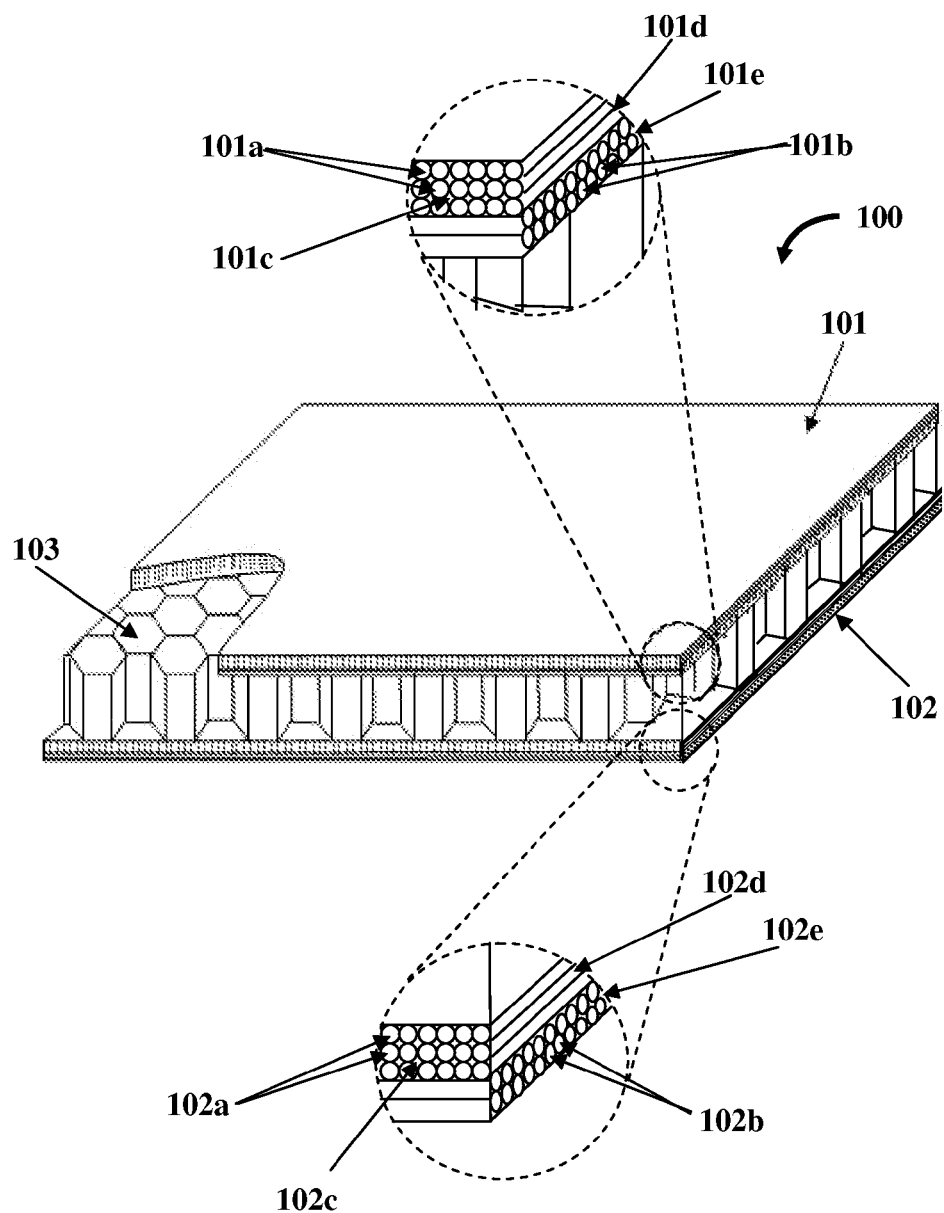
FIG. 1 illustrates a perspective view of a radiolucent patient table top.

FIG. 1 illustrates a perspective view of a radiolucent patient table top 100. The radiolucent patient table top 100 disclosed herein comprises a first face sheet 101, a second face sheet 102, and a carbon fiber honeycomb core 103. The first face sheet 101 comprises carbon fibers 101a and 101b in a first radiolucent plastic matrix 101c. The second face sheet 102 comprises carbon fibers 102a and 102b in a second radiolucent plastic matrix 102c. In an embodiment, the first plastic matrix 101c of the first face sheet 101 and the second plastic matrix 102c of the second face sheet 102 comprise, for example, a radiolucent epoxy resin. The carbon fiber honeycomb core 103 is disposed between the first face sheet 101 and the second face sheet 102. The first face sheet 101 and the second face sheet 102 sandwich the carbon fiber honeycomb core 103. The honeycomb core 103 comprises carbon fibers 103a embedded in a third radiolucent plastic matrix 103b as exemplarily illustrated in FIGS. 2-3. In an embodiment, the third radiolucent plastic matrix 103b of the honeycomb core 103 comprises, for example, a radiolucent phenolic resin or a radiolucent epoxy resin. In an embodiment, the first radiolucent plastic matrix 101c, the second radiolucent plastic matrix 102c, and the third radiolucent plastic matrix 103b are composed, for example, of a radiolucent thermoset or a thermoplastic.

In an embodiment, each of the first face sheet 101 and the second face sheet 102 further comprises two sets of unidirectional carbon fiber sheets 101d, 101e and 102d, 102e respectively, placed substantially orthogonally with respect to each other. In another embodiment, woven carbon fiber sheets may also be used; however, the woven carbon fiber sheets have lesser stiffness when compared to that of the unidirectional carbon fiber sheets 101d, 101e and 102d, 102e.

Figure 2:
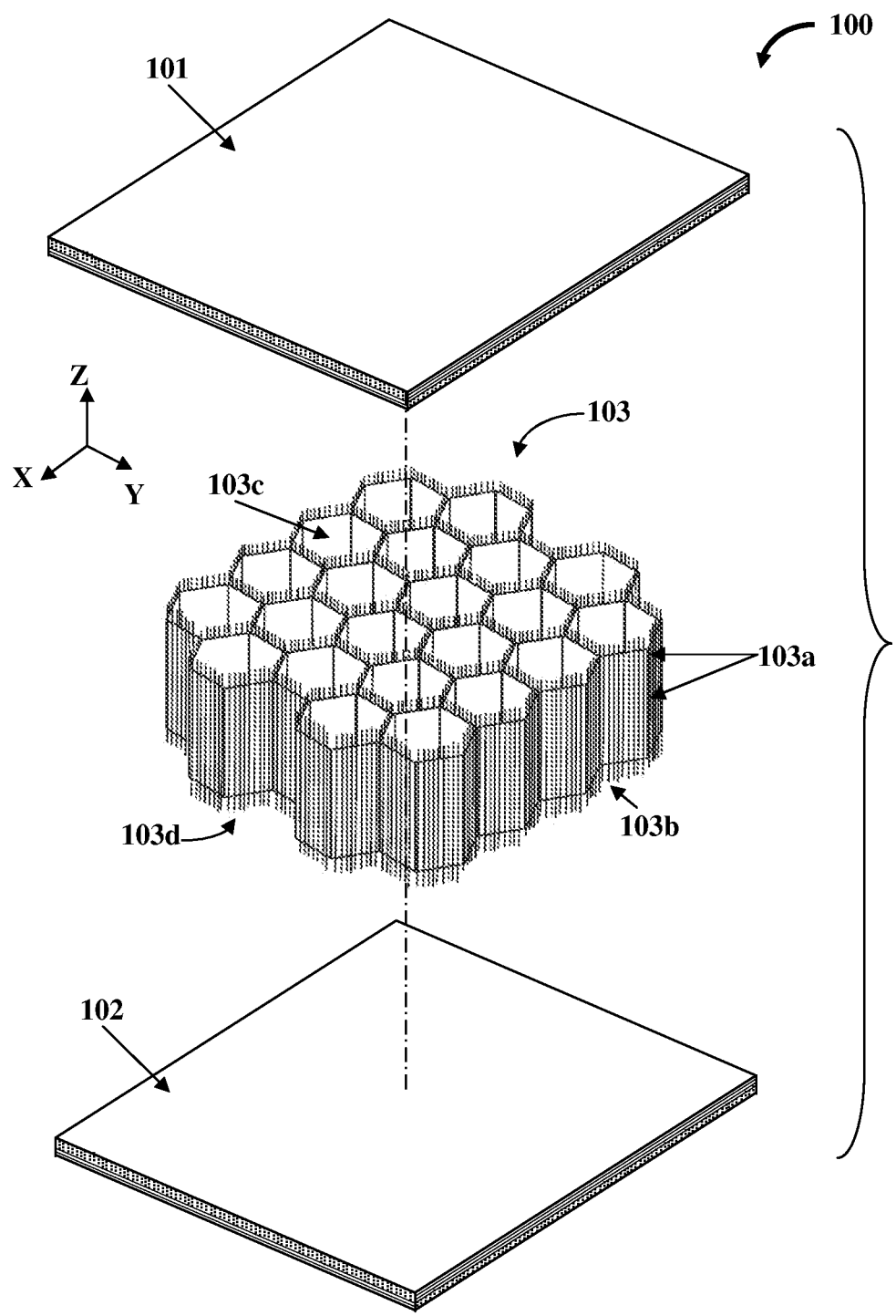
FIG. 2 exemplarily illustrates an exploded view of the radiolucent patient table top.

FIG. 2 exemplarily illustrates an exploded view of the radiolucent patient table top 100. The honeycomb core 103 disposed between the first face sheet 101 and the second face sheet 102 comprises carbon fibers 103a substantially unidirectional and perpendicular to a plane of the first face sheet 101 and the second face sheet 102. A substantial portion of the carbon fibers 103a of the honeycomb core 103 is unidirectional and oriented in a Z direction perpendicular to the plane of the first face sheet 101 and the second face sheet 102.

Figure 3:
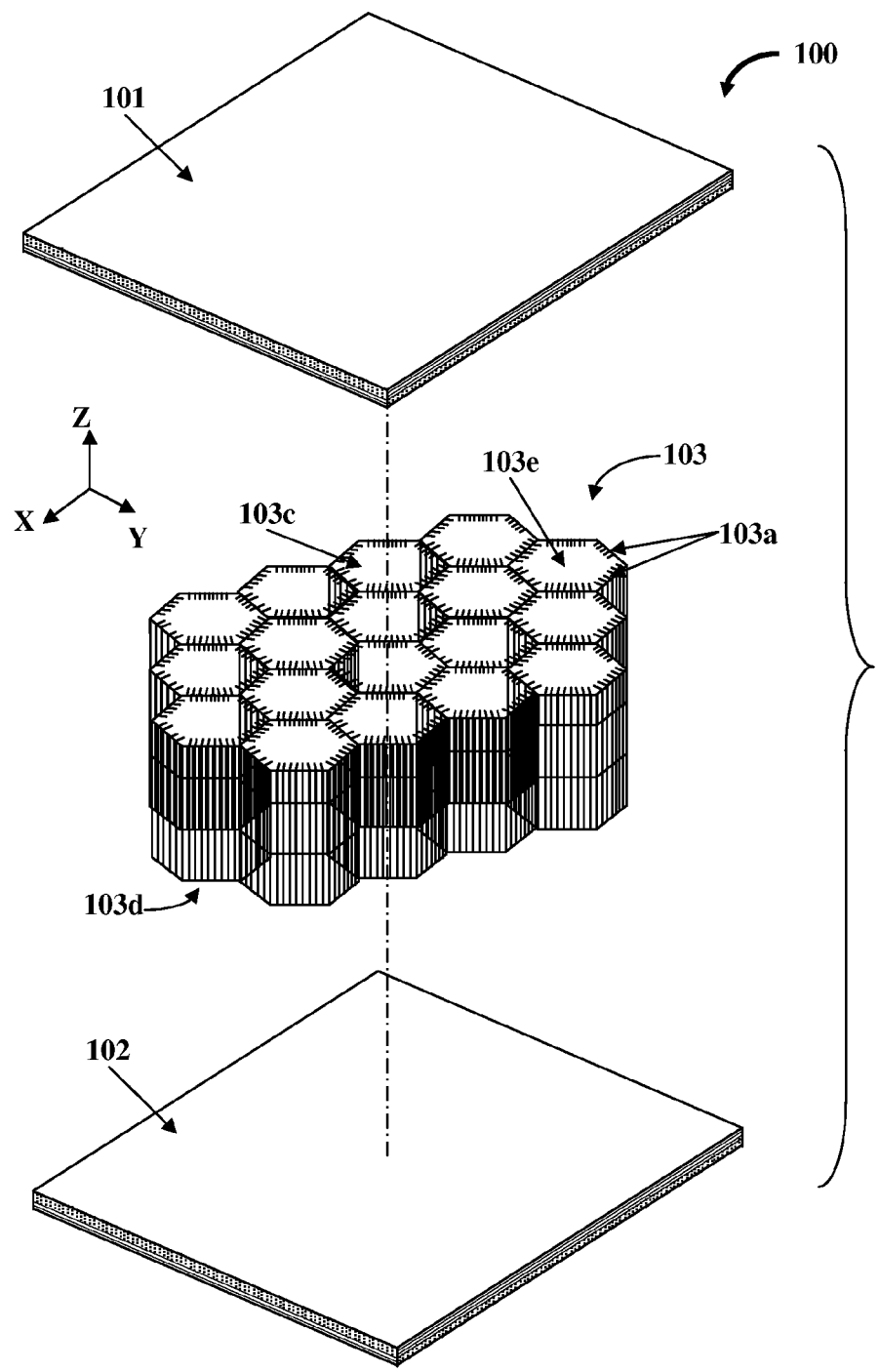
FIG. 3 exemplarily illustrates an exploded view of an embodiment of the radiolucent patient table top.

FIG. 3 exemplarily illustrates an exploded view of an embodiment of the radiolucent patient table top 100. In this embodiment, the carbon fibers 103a of the honeycomb core 103 are unidirectional and oriented in the Z direction perpendicular to the plane of the first face sheet 101 and the second face sheet 102, and additionally continued on the face 103e of the honeycomb core 103 to provide improved delamination resistance. Such a fiber orientation is disclosed in the co-pending patent application number 3671/CHENP/2014 titled "3D Fiber Composite", filed in the Indian Patent Office on 15 Apr. 2014, and non-provisional patent application Ser. No. 14/357,771 titled "3D Fiber Composite", filed in the United States Patent and Trademark Office on 13 May 2014.

The composition and performance of the radiolucent patient table top 100 is provided in the example below. The radiolucent patient table top 100 comprises a first face sheet 101 and a second face sheet 102, each of, for example, about 750 grams per square meter (gsm) in an epoxy resin matrix. The first face sheet 101 and the second face sheet 102 are bonded to a top surface 103c and a bottom surface 103d of a carbon fiber honeycomb core 103 exemplarily illustrated in FIGS. 2-3, of thickness, for example, about 24 mm. Each 750 gsm carbon fiber face sheet 101 and 102 further comprises 500 gsm carbon fibers in an epoxy matrix in a long axis along the length of the radiolucent patient table top 100 and 250 gsm carbon fibers in an epoxy matrix in a short axis along the breadth of the radiolucent patient table top 100. The carbon fiber honeycomb core 103 comprises unidirectional carbon fibers 103a in a phenolic resin matrix, yielding a core density of 1200 gsm for a 24 mm thick core. The first face sheet 101 and the second face sheet 102 are bonded to the top surface 103c and the bottom surface 103d of the carbon fiber honeycomb core 103, for example, using a 250 gsm layer of a radiolucent epoxy adhesive film. In this example, the total thickness of the radiolucent patient table top 100 adds up to approximately 1 inch. Such a radiolucent patient table top 100 has a radiolucency performance of, for example, 0.35 mm aluminum, and a deflection of, for example, less than 1 inch for a cantilever load of 200 kg along a span length of 75 cm. If a foam mattress is added on top of the radiolucent patient table top 100, the radiolucency of the radiolucent patient table top 100 may drop by an additional approximate 0.5 aluminum.

The method for manufacturing the radiolucent patient table top 100 is provided below. Unidirectional prepregs of, for example, about 250 gsm are manufactured by hot melt impregnation of carbon fibers in a radiolucent epoxy matrix. Careful attention must be paid to avoid the use of fillers that are radiolucent contaminants. An example of a radiolucent contaminant to be avoided is fumed silica. The 750 gsm carbon fiber face sheets 101 and 102 in an epoxy resin matrix, comprise two 250 prepregs along the greater length and one 250 gsm prepreg placed orthogonally over the width. A carbon fiber honeycomb core 103 with a cell size of, for example, about 5 mm in a phenolic resin matrix weighing, for example, about 1200 gsm for a 24 mm thickness is placed between the first face sheet 101 and the second face sheet 102, and two radiolucent epoxy adhesive films of 250 gsm each are introduced between the face sheets 101 and 102 and the top surface 103c and the bottom surface 103d of the carbon fiber honeycomb core 103 respectively. The carbon fiber honeycomb core 103 is manufactured in accordance with the manufacturing method disclosed in the co-pending patent application number 3671/CHENP/2014 titled "3D Fiber Composite" and U.S. non-provisional patent application Ser. No. 14/357,771 titled "3D Fiber Composite". The above sandwich structure is placed in a vacuum bag with a breather layer and heated in an oven over a two hour period ramping up to 80° Celsius (C), holding for half an hour, ramping up to 120° C., holding for 45 minutes, and then cooling down to room temperature.

The foregoing examples have been provided merely for the purpose of explanation and are in no way to be construed as limiting of the radiolucent patient table top 100 and the method of manufacture disclosed herein. While the radiolucent patient table top 100 and the method of manufacture have been described with reference to various embodiments, it is understood that the words, which have been used herein, are words of description and illustration, rather than words of limitation. Further, although the radiolucent patient table top 100 and the method of manufacture have been described herein with reference to particular means, materials, and embodiments, the radiolucent patient table top 100 and the method of manufacture are not intended to be limited to the particulars disclosed herein; rather, the radiolucent patient table top 100 and the method of manufacture extend to all functionally equivalent structures, methods and uses, such as are within the scope of the appended claims. Those skilled in the art, having the benefit of the teachings of this specification, may effect numerous modifications thereto and changes may be made without departing from the scope and spirit of the radiolucent patient table top 100 and the method of manufacture disclosed herein in their aspects.

I claim:

1. A radiolucent patient table top comprising:
    a first face sheet comprising carbon fibers in a first plastic matrix, wherein said first plastic matrix is radiolucent;
    a second face sheet comprising carbon fibers in a second plastic matrix, wherein said second plastic matrix is radiolucent, and wherein each of said first face sheet and said second face sheet further comprises two sets of unidirectional carbon fiber sheets placed substantially orthogonally with respect to each other; and
    a honeycomb core disposed between said first face sheet and said second face sheet, wherein said honeycomb core comprises carbon fibers embedded in a third plastic matrix, wherein said third plastic matrix is radiolucent, and wherein said carbon fibers in said honeycomb core are substantially unidirectional and perpendicular to a plane of said first face sheet and said second face sheet.

2. The radiolucent patient table top of claim 1, wherein said first plastic matrix of said first face sheet and said second plastic matrix of said second face sheet comprise a radiolucent epoxy resin.

3. The radiolucent patient table top of claim 1, wherein said third plastic matrix of said honeycomb core comprises one of a radiolucent phenolic resin and a radiolucent epoxy resin.

* * * * *